(12) United States Patent
Campbell

(10) Patent No.: US 7,473,273 B2
(45) Date of Patent: Jan. 6, 2009

(54) STENT ASSEMBLY WITH THERAPEUTIC AGENT EXTERIOR BANDING

(75) Inventor: Todd Campbell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 808 days.

(21) Appl. No.: 10/056,418

(22) Filed: Jan. 22, 2002

(65) Prior Publication Data
US 2003/0139800 A1 Jul. 24, 2003

(51) Int. Cl.
*A61F 2/06* (2006.01)

(52) U.S. Cl. ............ 623/1.15; 623/1.44; 623/1.46

(58) Field of Classification Search ........... 623/1.12, 623/1.15, 1.16, 1.42, 1.43, 1.44, 1.46
See application file for complete search history.

(56) References Cited

U.S. PATENT DOCUMENTS

| | | | |
|---|---|---|---|
| 4,739,762 A | 4/1988 | Palmaz | |
| 4,950,227 A | 8/1990 | Savin et al. | |
| 5,133,732 A | 7/1992 | Wiktor | |
| 5,292,331 A | 3/1994 | Boneau | |
| 5,383,928 A | 1/1995 | Scott et al. | |
| 5,421,955 A | 6/1995 | Lau et al. | |
| 5,628,784 A | 5/1997 | Strecker | |
| 5,674,242 A | 10/1997 | Phan et al. | |
| 5,779,732 A | 7/1998 | Amundson | |
| 5,836,965 A | 11/1998 | Jendersee et al. | |
| 6,019,789 A | 2/2000 | Dinh et al. | |
| 6,090,127 A | 7/2000 | Globerman | |
| 6,096,070 A * | 8/2000 | Ragheb et al. | 623/1.39 |
| 6,159,229 A | 12/2000 | Jendersee et al. | |
| 6,355,055 B1 * | 3/2002 | Waksman et al. | 623/1.13 |
| 6,451,050 B1 * | 9/2002 | Rudakov et al. | 623/1.15 |
| 6,530,950 B1 * | 3/2003 | Alvarado et al. | 623/1.13 |
| 2001/0020181 A1 * | 9/2001 | Layne | 623/1.13 |

FOREIGN PATENT DOCUMENTS

WO    WO 00/12147    3/2000

* cited by examiner

*Primary Examiner*—Julian W Woo
*Assistant Examiner*—Victor X Nguyen

(57) ABSTRACT

The stent assembly with exterior banding for delivery of therapeutic agents of the present invention comprises a stent and drug coated bands located circumferentially around the stent. The width of the bands allows free flow of blood or other fluids to side branch lumens within the body. Positioning the bands on the abluminal surface prevents the intrusion of the bands into the inner diameter of the stent, thus optimizing patency. The therapeutic agent can vary from band to band, or different therapeutic agents can be included at different radial locations within the band. In an alternate embodiment, the stent assembly can comprise a stent and one or more helical wraps around the stent, the helical wraps including one or more therapeutic agent.

5 Claims, 6 Drawing Sheets

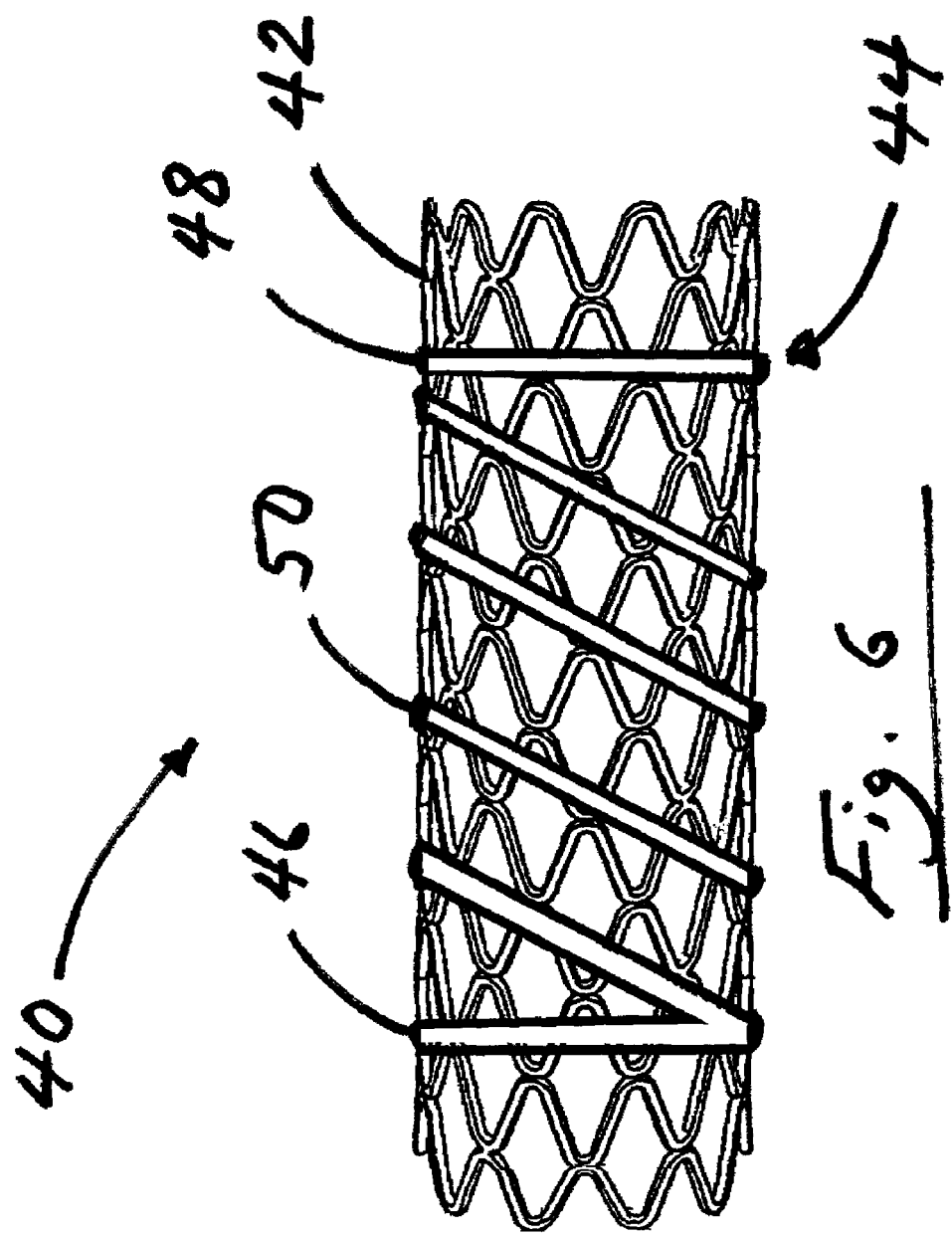

STENT ASSEMBLY WITH THERAPEUTIC AGENT EXTERIOR BANDING

TECHNICAL FIELD

The technical field of this disclosure is medical implant devices, particularly, an expandable stent assembly having exterior banding for delivery of therapeutic agents.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed.

Stents have been used with coatings to deliver drug or other therapy at the site of the stent, but have certain limitations. Typically, a thin coating is required so that the coating can adhere to the metal or other material forming the stent and so that the stent profile remains small. This limits the amount of drug that can be loaded within the coating. It is also difficult to manufacture and deliver a stent with a uniform coating. This creates uncertainty about the dosage of drug delivered to the patient and increases the cost because additional drug must be loaded to assure an effective dose. Typically, the coating is applied over the whole stent. This results in medication of normal, undamaged tissue at the end of the stent, where treatment may not be necessary or desirable. The uniform coating also delivers the same therapy inside and outside the stent, and over the length of the stent.

Alternative strategies for delivering drugs or other therapies at the site of the stent have included sheaths enclosing all or almost all of the stent. The stent supports the sheath and maintains the sheath against the lumen wall. Problems can arise if the sheath covers side branch arteries, vessels, or other lumens extending from the main lumen in which the stent is installed. The sheath can reduce blood flow to or from the side branch and deliver medication into the side branch where it is unnecessary.

U.S. Pat. No. 6,019,789 to Dinh, et al. discloses use of a stent as a scaffold or structural member for carrying a polymer stent or sheath which preferably contains a therapeutic agent.

U.S. Pat. No. 5,674,242 to Phan et al. discloses an endoprosthetic device for insertion at a vascular site composed of a structural member carrying a polymer member having an embedded therapeutic compound. The polymer member is formed of a shape-memory polymer for expansion upon exposure to a selected stimulus. The polymer member is coextensive with the structural member, or, in other embodiments, the polymer member encases the structural member and, in its contracted state, is effective to restrain the structural member in its contracted state.

U.S. Pat. No. 5,383,928 to Scott et al. discloses a sheath for encompassing at least a portion of a stent to locally deliver a drug to an arterial wall or lumen into which the stent has been inserted, comprising a polymer and a drug incorporated within the polymer, the polymer sheath encompassing at least a portion of the stent and having a thickness to allow controlled release of the drug.

WIPO International Publication No. WO00/12147 to Yang et al. discloses a device adapted for mounting on a stent, the device comprising a sheath being made of polymeric material that includes drugs such as pharmaceutical agent(s) or radioactive agent(s) for delivery to an implant site. The sheath includes a main body of generally tubular shape, and may include mounting means for attaching same to stent. The device may have a slit therein, and may comprise a helical coil, a cylinder or any other suitable shape or design which fits a particular stent. The sheath may include a coating or coatings thereon, containing drugs, surgical adhesives or a combination thereof.

During the procedure, the balloon stent catheter is advanced through a network of tortuous blood vessels. Furthermore, the balloon stent catheter also may encounter narrowed lumens or lumens that are obstructed. Once at the desired site, the balloon is inflated and expands the stent to a final diameter. After deployment, the stent remains in the vessel and the balloon catheter is removed.

The position of the stent on the balloon should be maintained while the balloon stent catheter is moved longitudinally through the network of vessels. In moving to the implant site, the stent may be shifted on the balloon so that the stent may not expand fully along its length or completely dislodged from the balloon. Current strategies for retaining the stent on the balloon include: plastically deforming the stent so that it is crimped onto the balloon; increasing the friction forces between the stent and balloon by modifying the balloon through heat, pressure, or chemical or adhesive means; adding retainers that physically prevent the stent movement; and combinations thereof.

U.S. Pat. No. 4,950,227 to Savin discloses a strategy for stent retention that utilizes end caps mounted on the catheter. The end caps are adapted to temporarily engage the ends of the stent while permitting the stent ends to release when the stent is expanded.

U.S. Pat. Nos. 5,836,965 and 6,159,229 issued Dec. 12, 2000 to Jendersee et al. discloses a strategy for stent retention utilizing a heating process to deform the balloon about the stent while the balloon is heated and preferably pressurized. The balloon expands around and within gaps of the stent causing it to adhere. The balloon continues to adhere as it is cooled and its shape is set. Furthermore, retainers may be placed at the distal and/or proximal ends of the stent.

It would be desirable to have a stent assembly with exterior banding for delivery of therapeutic agents that would overcome the above disadvantages.

SUMMARY OF THE INVENTION

One aspect of the present invention provides a stent assembly which avoids side branch vessel blockage by a sheath.

Another aspect of the present invention provides a stent assembly with increased drug storage capacity.

Another aspect of the present invention provides a stent assembly affording precise control over drug delivery.

Another aspect of the present invention provides a stent assembly allowing delivery of different drugs at different axial and radial locations.

Another aspect of the present invention provides a stent assembly allowing delivery of different drugs to the vascular wall and the blood.

Another aspect of the present invention provides a stent assembly with the stent firmly secured to the balloon.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 6 shows an alternate embodiment of an expanded stent assembly with a helical wrap made in accordance with the present invention.

DETAILED DESCRIPTION OF THE PRESENTLY PREFERRED EMBODIMENTS

The stent assembly with exterior banding for delivery of therapeutic agents of the present invention comprises a stent and drug coated bands located circumferentially around the stent. The width of the bands allows free flow of blood or other fluids to side branch lumens within the body. Positioning the bands on the abluminal surface prevents the intrusion of the bands into the inner diameter of the stent, thus optimizing patency. The therapeutic agent can vary from band to band, or different therapeutic agents can be included at different radial locations within the band. In an alternate embodiment, the stent assembly can comprise a stent and one or more helical wraps around the stent, the helical wraps including one or more therapeutic agent.

Figure 1:
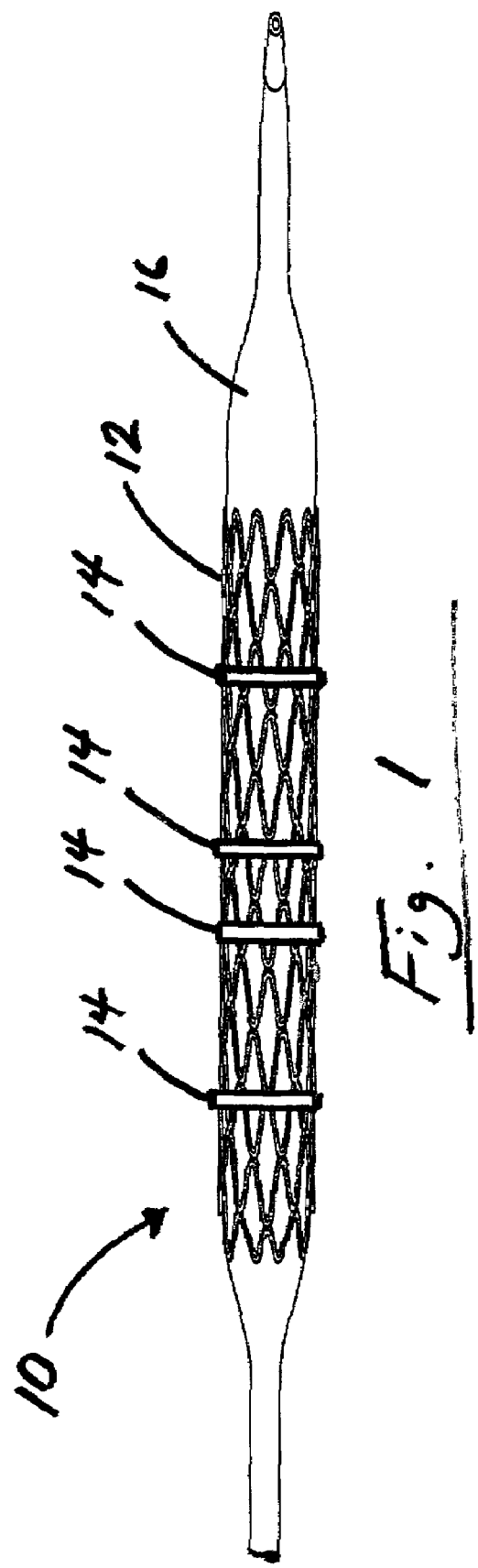
FIG. 1 shows a stent assembly with bands made in accordance with the present invention.

FIG. 1 shows a stent assembly with bands made in accordance with the present invention. The stent assembly 10 comprises a stent 12 and at least one band 14 removably located around the stent 12. The stent assembly 10 is shown before implantation in a patient, crimped on balloon 16. The bands 14 contain therapeutic agents which elute from the bands 14. Different numbers of bands 14 can be used as desired for a particular therapy or dosage and the bands 14 can be located at different axial locations on the stent 12 to apply the therapeutic agent where required in the body lumen. Use of a number of bands 14 or varying the width of bands 14 can provide increased surface area for administering the therapeutic agents over the surface available on the stent 12 if a coating were to be used. Different therapeutic agents can be used in one or more of the bands 14 to provide different therapies. For example, a band with an anti-inflammatory could be provided on the proximal portion of the stent to reduce inflammation from the stent at the implantation site and a band with an anti-thrombotic could be installed on the distal portion of the stent to provide the anti-thrombotic throughout the blood stream.

The stent 12 is conventional and can be made of a wide variety of medical implantable materials, such as stainless steel, nitinol, tantalum, ceramic, nickel, titanium, aluminum or polymeric materials. The stent 12 can be formed through various methods as well. The stent 12 can be welded, molded, or consist of filaments or fibers which are wound or braided together in order to form a continuous structure. The scaffolding of the stent 12 can be substantially continuous to provide circumferential support to the bands 14. Typically, the stent 12 can have a crimped diameter of 1 mm to 8 mm and an expanded diameter of 2 mm to 25 mm, depending on the particular application.

The bands 14 can be made of a polymer containing a drug or therapeutic agent. After the stent assembly 10 is inserted in a body lumen, the therapeutic agent elutes from the polymer into the lumen or the surrounding tissue. The polymer can be biodegradable or non biodegradable, depending on the particular application.

The drug or therapeutic agent carried by the polymer of the bands 14 can be varied depending on the body lumen involved, the result desired, and the therapy indicated. Combinations of therapeutic agents can be used. Examples of therapeutic agents that can be used in the bands 14 are thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

The bands 14 can be made of various polymers. The polymer can be elastic to grip the stent 12 so that the bands 14 remain in place during implantation. Further, the bands 14 can help compress the stent 12 onto the balloon 16 so that the stent 12 remains in place on the balloon 16 during implantation. The bands 14 can be free floating on the stent 12, so that there is no stress concentration within the band 14 that might cause the band 14 to break as the stent 12 is expanded. Typically, the diameter of the stent 12 increases by two to eight times during expansion, so the band 14 must be able to stretch proportionately. The bands 14 are sized so that the bands 14 permit free flow to side branch lumens. For example, during PTCA (percutaneous transluminal coronary angioplasty) with stent implantation, the bands 14 are sized to allow free blood flow through side branch arteries at the implantation site. Typically, in the predeployed state, the bands 14 can be about 0.200 inches wide and 0.100 inches thick, but can range from 0.010 to 0.500 inches wide and 0.010 to 0.250 inches thick.

The bands 14 can be made of various polymers, such as a single polymer, a copolymer blend, a polymer mixture, a copolymer mixture, or a polymer-copolymer mixture. The polymer can be a biostable polymer, a bioabsorbable polymer, or a biomolecular polymer. Suitable biostable or bioabsorbable polymers can be poly(L-lactic acid), polycaprolactone, poly(lactide-co-glycolide), poly(hydroxybutyrate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes. Suitable biomolecular polymers can be fibrin, fibrinogen, cellulose, starch, collagen or hyaluronic acid. Other suitable polymers can be polyurethanes, silicones, polyesters, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as nylon 66 and polycaprolactam; alkyd resins; polycarbonates; polyoxymethylenes; polyimides; polyethers; epoxy resins; polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. Those skilled in the art will recognize that various polymers and polymer mixtures are suitable for particular applications, depending on the desired elasticity and ability to carry the particular therapeutic agents.

The bands 14 can be installed on the stent 12 by slipping the bands 14 over the stent 12 after the balloon 16 is installed in the stent 12. If the band 14 is multi-layered as described for FIG. 3 below, the band 14 can be oriented so that a first layer is adjacent to the stent 12 and a second layer is away from the stent 12. Different numbers of bands 14 can be used as desired for a particular therapy or dosage and the bands 14 can be located at different axial locations on the stent 12 to apply the therapeutic agent where required in the body lumen. The bands 14 can be installed away from the ends of the stent 12 to avoid treatment of normal, undamaged tissue at the end of the stent.

Figure 2:
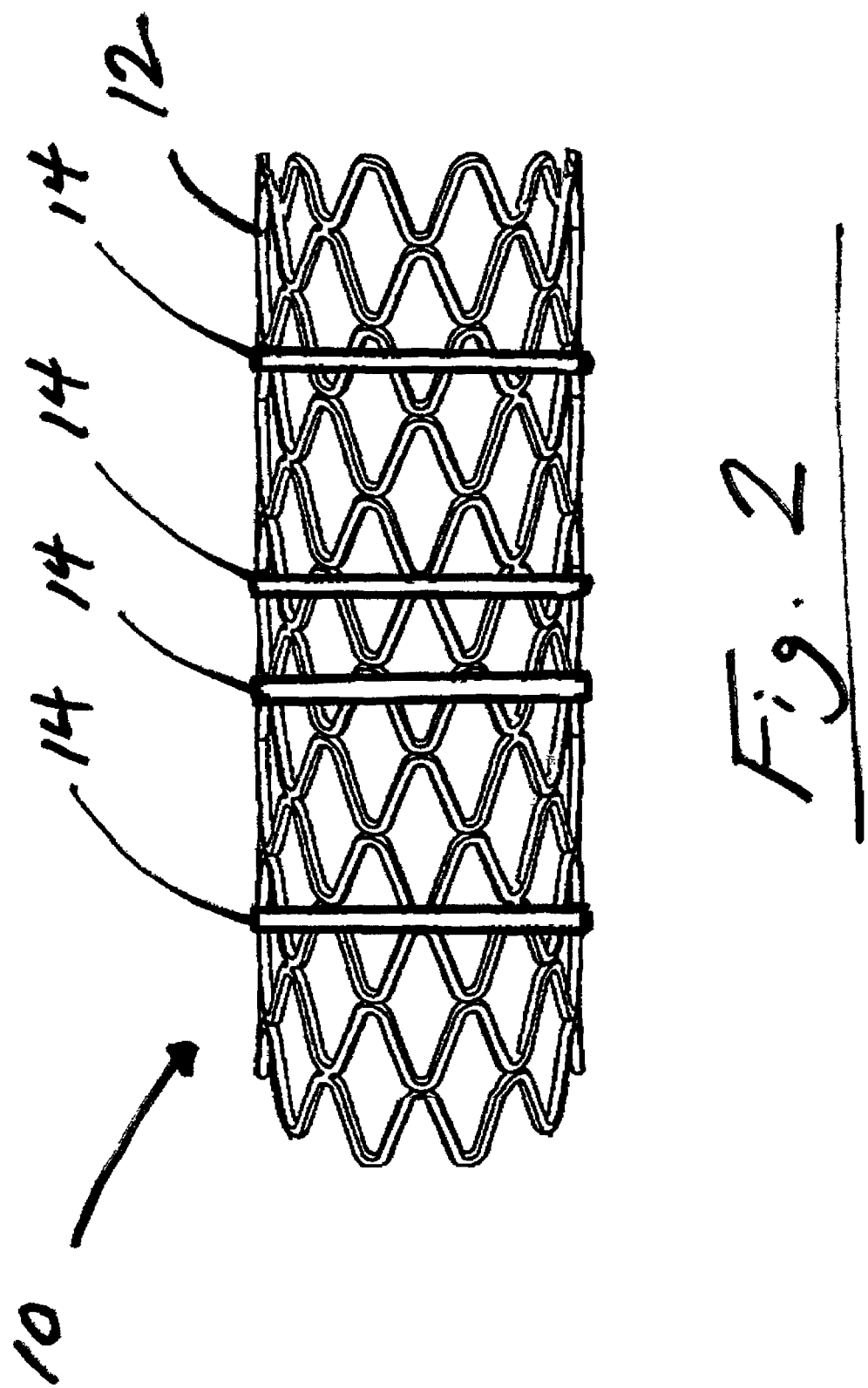
FIG. 2 shows an expanded stent assembly with bands made in accordance with the present invention.

FIG. 2, in which like elements have like reference numbers with FIG. 1, shows an expanded stent assembly with bands made in accordance with the present invention. The stent assembly 10 comprises a stent 12 and at least one band 14 removably located around the stent 12. As shown in the expanded condition after implantation, the exterior of the bands 14 are held against the wall of the body lumen by the stent 12 and the interior of the bands 14 are exposed to the body lumen and any fluid or other material within the body lumen. The thin width of the bands 14 avoids interference with flow through any side branch lumens covered by the stent 12.

Figure 3:
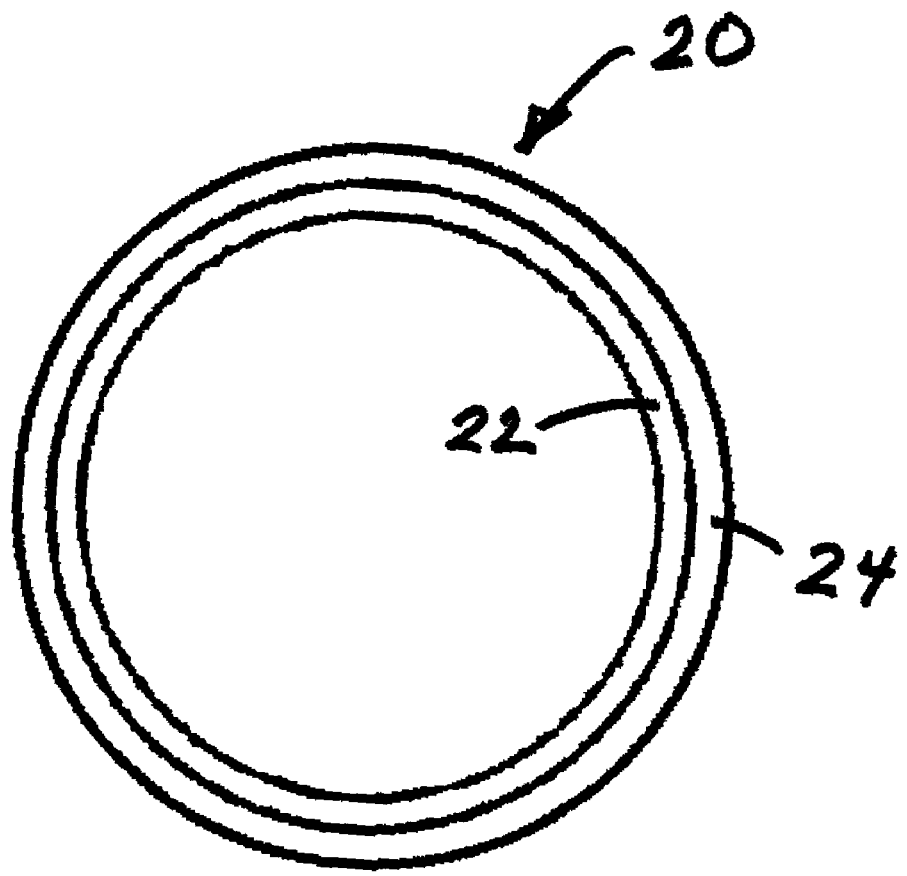
FIG. 3 shows a multi-layered band made in accordance with the present invention.

FIG. 3 shows a multi-layered band made in accordance with the present invention. The multi-layered band can provide different therapies to the lumen side and the lumen wall or provide different therapies over time. The band 20 comprises a first layer 22 and a second later 24 and is oriented abluminally around a stent so that the first layer 22 is near the stent and the second layer 24 is away from the stent. The first layer 22 can be made of one polymer containing one therapeutic agent and the second layer 24 can be made of the same or a different polymer with the same or a different therapeutic agent. For example, the first layer 22 could be a non-biodegradable polymer while the second layer 24 could be a biodegradable polymer: The therapeutic agent in the first layer 22 would be present long term while the therapeutic agent in the second layer 24 would be present short term. In another example, the first layer 22 could contain an anti-thrombotic while the second layer 24 could contain an anti-inflammatory. The first layer 22 in closest proximity to the lumen could release the anti-thrombotic therapy, while the second layer 24 in closest proximity to the vessel wall could release the anti-inflammatory therapy.

It will be appreciated by those skilled in the art that bands with more than two layers will also be useful and advantageous. For example, a three layer band could be oriented abluminally around a stent with an inner layer near the stent, an outer layer away from the stent, and a middle layer between the inner layer and the outer layer. The inner layer could provide one therapeutic agent, the outer layer could be biodegradable and provide a different therapeutic agent that would be most useful immediately after stent implantation, and the middle layer could elute another therapeutic agent after the outer layer biodegrades. The combinations of layers described are exemplary only and are not limitations on the scope of the present invention.

Figure 4:
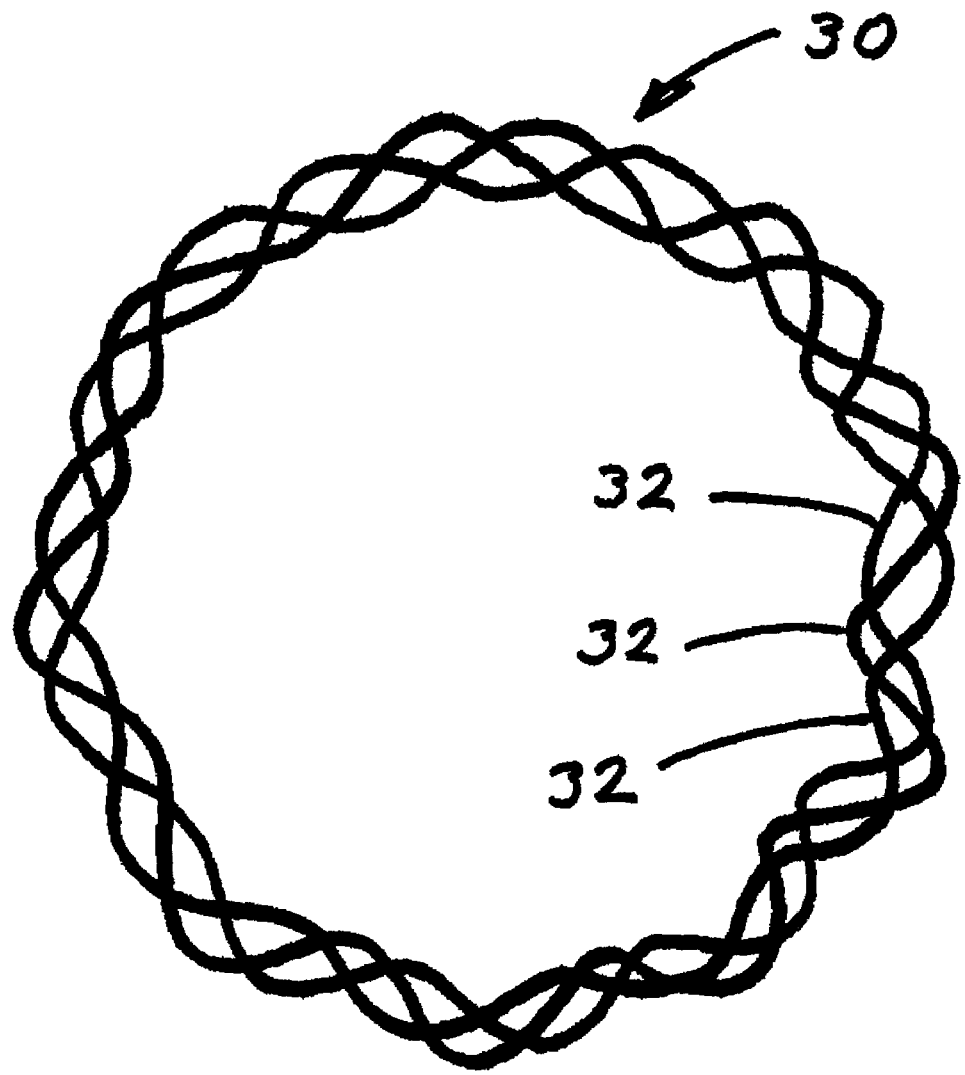
FIG. 4 shows a braided band made in accordance with the present invention.

FIG. 4 shows a braided band made in accordance with the present invention. The band 30 comprises a plurality of interwoven filaments 32. The filaments 32 can be kept as separate interwoven fibers or can be bonded together into a single unit. In one embodiment, the filaments 32 can be made of different polymers. In another embodiment, the filaments 32 can contain different therapeutic agents. The use of a plurality of filaments 32 provides fine control of the release rate and the dosage of a mixture of therapeutic agents. The interwoven filaments also maximize the surface area available to elute the therapeutic agents. Typically, the individual filaments 32 can have a diameter of about 0.010 inches with a range from 0.005 to 0.500 inches. Typically, ten filaments 32 can form the band 30 but the as few as two or as many as fifty or more could be used.

Figure 5:
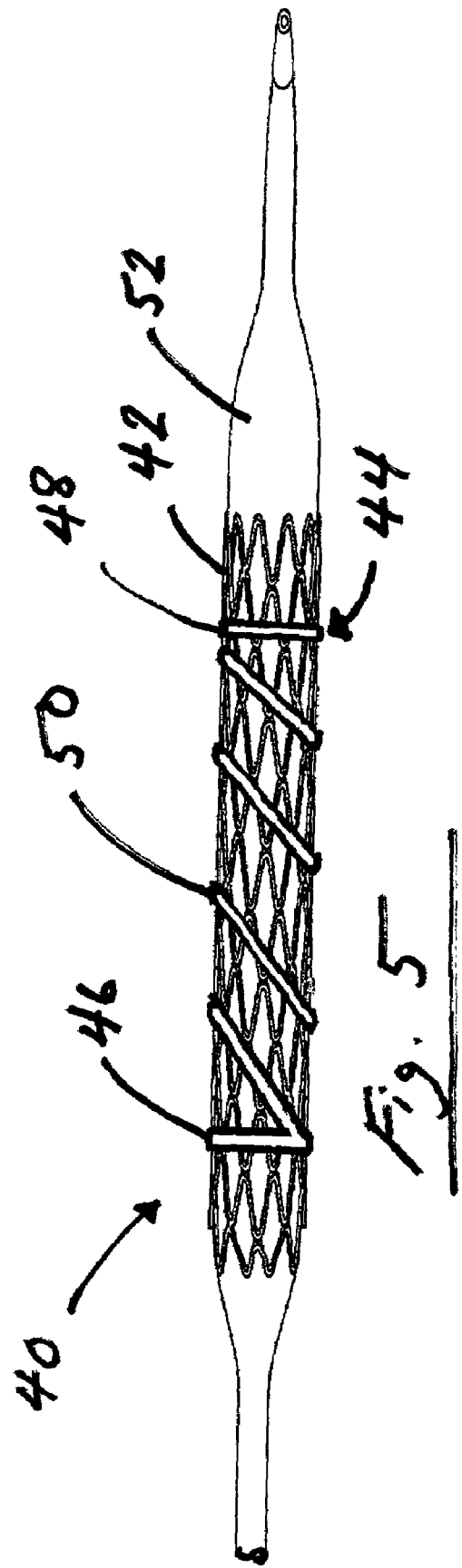
FIG. 5 shows an alternate embodiment of a stent assembly with a helical wrap made in accordance with the present invention.

FIG. 5 shows an alternate embodiment a stent assembly with helical wrap made in accordance with the present invention. The stent assembly 40 comprises a stent 42 with a helical wrap 44 removably located around the stent 42. The helical wrap 44 further comprises a first anchor 46 and a second anchor 48, with a connector 50 between the first anchor 46 and the second anchor 48. In another embodiment, a plurality of connectors 50 can be used to provide additional polymer for drug loading. The first anchor 46 and the second anchor 48 affix the helical wrap 44 to the stent 42. In another embodiment, the first anchor 46 and the second anchor 48 can be omitted and the ends of the connector 50 attached directly to the stent 42. The stent assembly 40 is shown before implantation in a patient, crimped on balloon 52. The helical wrap 44 contains therapeutic agents which elute from the helical wrap 44. Changing the pitch of the wrapping of the connector 50 can change the surface area available for administering the therapeutic agents. Different therapeutic agents can be used over the length of the connector 50 to provide different therapies axially along the stent assembly 40. The helical wrap 44 is sized so that the helical wrap 44 permits free flow to side branch lumens. Typically, in the predeployed state, the helical wrap 44 can be about 0.200 inches wide and 0.100 inches thick, but can range from 0.010 to 0.500 inches wide and 0.010 to 0.250 inches thick.

The helical wrap 44 can be made of the same polymers and contain the same therapeutic agents as discussed for the stent assembly of FIG. 1. In one embodiment, the helical wrap 44 can be multi-layered as discussed for the multilayered band of FIG. 3. One side of the helical wrap 44 can follow the outside of the stent 42, so one layer always faces the lumen side and another layer always faces the lumen wall. In another embodiment, the helical wrap 44 can be made of interwoven filaments as discussed for the braided band of FIG. 4.

FIG. 6, in which like elements have like reference numbers with FIG. 5, shows an alternate embodiment of an expanded stent assembly with a helical wrap made in accordance with the present invention. The stent assembly 10 comprises a stent 12 and a helical wrap 44 removably located around the stent 12. As shown in the expanded condition after implantation, the exterior of the helical wrap 44 is held against the wall of the body lumen by the stent 42 and the interior of the helical wrap 44 is exposed to the body lumen and any fluid or other material within the body lumen. The thin cross-section of the helical wrap 44 avoids interference with flow through any side branch lumens covered by the stent 42.

It is important to note that FIGS. 1-6 illustrate specific applications and embodiments of the present invention, and is not intended to limit the scope of the present disclosure or claims to that which is presented therein. For example, many combinations of polymers and therapeutic agents are possible for specific therapies. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent assembly for implantation in a body lumen comprising:
   a stent; and
   a plurality of bands circumferentially wrapped around the stent, the plurality of bands including at least a first band and a second band, the width of each of the bands being substantially less than the diameter of the stent;
   wherein the bands further comprise a polymer containing a therapeutic agent, the bands elastically gripping the stent; and
   wherein individual bands of the plurality of bands contain different therapeutic agents, the first band containing a first therapeutic agent and the second band containing a second therapeutic agent, the first therapeutic agent being different than the second therapeutic agent.

2. The stent assembly of claim 1 wherein the stent has a proximal portion and a distal portion, the first band being disposed on the proximal portion and the second band being disposed on the distal portion.

3. A stent assembly for implantation in a body lumen comprising:
   a stent; and
   a plurality of bands circumferentially wrapped around the stent, the plurality of bands including at least a first band and a second band, the width of each of the bands being substantially less than the diameter of the stent;
   wherein the bands further comprise a polymer containing a therapeutic agent, the bands elastically gripping the stent; and
   wherein individual bands of the plurality of bands are made of different polymers, the first band being made of a first polymer and the second band being made of a second polymer, the first polymer being different than the second polymer.

4. A stent assembly for implantation in a body lumen comprising:
   a stent; and
   at least one band circumferentially wrapped around the stent, the width of the band being substantially less than the diameter of the stent;
   wherein the band further comprises a polymer containing a therapeutic agent, the band elastically gripping the stent, the polymer comprising a first polymer and a second polymer, the first polymer being different than the second polymer; and
   wherein the band further comprises a first layer and a second layer, the first layer located circumferentially around the stent, and the second layer attached circumferentially around the first layer, the first layer being made of the first polymer and the second layer being made of the second polymer.

5. A stent assembly for implantation in a body lumen comprising:
   a stent; and
   at least one band circumferentially wrapped around the stent, the width of the band being substantially less than the diameter of the stent;
   wherein the band further comprises a polymer containing a therapeutic agent, the band elastically gripping the stent, the therapeutic agent comprising a first therapeutic agent and a second therapeutic agent, the first therapeutic agent being different than the second therapeutic agent; and
   wherein the band further comprises a first layer and a second layer, the first layer located circumferentially around the stent, and the second layer attached circumferentially around the first layer, the first layer containing the first therapeutic agent and the second layer containing the second therapeutic agent.

* * * * *